US008703753B2

(12) United States Patent
Sredni et al.

(10) Patent No.: US 8,703,753 B2
(45) Date of Patent: Apr. 22, 2014

(54) USE OF TELLURIUM COMPOUNDS FOR THE TREATMENT OF ACTINIC KERATOSIS

(75) Inventors: Benjamin Sredni, Kfar-Saba (IL); Michael Albeck, Ramat-Gan (IL)

(73) Assignee: Biomas Ltd., Kfar-Saba (IL)

( * ) Notice: Subject to any disclaimer, the term of this patent is extended or adjusted under 35 U.S.C. 154(b) by 781 days.

(21) Appl. No.: 12/517,222

(22) PCT Filed: Sep. 14, 2006

(86) PCT No.: PCT/IL2006/001080
§ 371 (c)(1),
(2), (4) Date: Jun. 2, 2009

(87) PCT Pub. No.: WO2007/032009
PCT Pub. Date: Mar. 22, 2007

(65) Prior Publication Data
US 2010/0150869 A1    Jun. 17, 2010

Related U.S. Application Data

(60) Provisional application No. 60/716,923, filed on Sep. 15, 2005.

(51) Int. Cl.
*A61K 31/33* (2006.01)
*A61K 31/095* (2006.01)

(52) U.S. Cl.
USPC .......................................... 514/183; 514/706

(58) Field of Classification Search
None
See application file for complete search history.

(56) References Cited

U.S. PATENT DOCUMENTS

| 4,752,614 | A | * | 6/1988 | Albeck et al. ................. 514/450 |
| 4,761,490 | A | | 8/1988 | Albeck et al. |
| 4,764,461 | A | | 8/1988 | Albeck et al. |
| 4,929,739 | A | | 5/1990 | Sredni et al. |
| 4,962,207 | A | | 10/1990 | Albeck et al. |
| 5,093,135 | A | * | 3/1992 | Albeck et al. ................. 424/650 |
| 5,102,908 | A | | 4/1992 | Albeck et al. |
| 5,213,899 | A | | 5/1993 | Lucas |
| 6,472,381 | B1 | | 10/2002 | Albeck et al. |
| 7,045,150 | B2 | | 5/2006 | Strassmann et al. |
| 2009/0269289 | A1 | | 10/2009 | Sredni et al. |

FOREIGN PATENT DOCUMENTS

| WO | WO 2007/032009 | 3/2007 |
| WO | WO 2007/032010 | 3/2007 |

OTHER PUBLICATIONS

Sredni et al. J. Natl. Cancer Inst., 1996, vol. 88, pp. 1276-1284.*
Yamamura et al. J. Clin. Invest., 1993, vol. 91, pp. 1005-1010.*
Kim et al. The Journal of Immunology, 1995, vol. 155, pp. 2240-2247.*
Geisse et al. J. Am. Acad. Dermatol., 2004, vol. 50, pp. 722-733.*
International Search Report and the Written Opinion Dated Apr. 3, 2007 From the International Searching Authority Re.: Application No. PCT/IL06/01081.
International Search Report and the Written Opinion Dated Jul. 21, 2008 From the International Searching Authority Re.: Application No. PCT/IL06/01080.
Lima et al. "A Novel Organotellurium Compound (RT-01) as a New Antileishmanial Agent", Korean Journal of Parasitology, 47(3): 213-218, Sep. 2009.
Persike et al. "Protective Effect of the Organotelluroxetane RF-07 in Pilocarpine-Induced Status Epilepticus", Neurobiology of Disease, 31: 120-126, 2008.
International Preliminary Report on Patentability Dated Jan. 2, 2008 From the International Preliminary Examining Authority Re.: Application No. PCT/IL06/01081.
Kalechman et al. "Role of Endogenous Cytokines Secretion in Radioprotection Conferred by the Immunomodulator Ammonium Trichloro(Dioxyethylenc-0-0')Tellurate", Blood, 85(6): 1555-1561, 1995. Abstract, p. 1555, col. 1, Lines 1-4, 6-15, p. 1559, col. 1, Lines 6-9, 12-20, col. 2, Lines 1-10.
U.S. Appl. No. 60/610,660, filed Sep. 17, 2004.
Montero et al., AS-101: a modulator of in vitro T-cell proliferation. Anticancer Drugs, 351-354, Jun. 1993.
Kozenitzky et al., Immunomodulatory effects of AS101 on interleukin-2 production and T-lymphocyte function of lymphocytes treated with psoralens and ultraviolet A. Photodermatol Photoimmunol Photomed Feb. 1992.
Blank et al., The effect of the immunomodulator agent AS101 on interleukin-2 production in systemic lupus erythematosus (SLE) induced in mice by a pathogenic anti-DNA antibody, Clin Exp Immunol, 79:443-447, Mar. 1990.
Sredni et al., The immunomodulator AS101 administered orally as a chemoprotective and radioprotective agent. Int J Immunopharmacol May 1992.
Nyska et al., Toxicity study in rats of a tellurium based immunomodulating drug, AS-101: a potential drug for AIDS and cancer patients. Arch Toxicol, 63:386-393, 1989.
Kalechman et al., Use and mechanism of action of AS101 in protecting bone marrow colony forming units-granulocytemacrophage following purging with ASTA-Z 7557, Cancer Res, 51:5614-5620, Oct. 15, 1991.
Vonsover et al., Inhibition of the reverse transcriptase activity and replication of human immunodeficiency virus type 1 by AS 101 in vitro, AIDS Res Hum Retroviruses. 8(5):613-23, 1992.
Strassmann et al., the immunomodulator AS-101 inhibits IL-10 release and arguments TNFa and IL-1α release by mouse and human mononuclear phagocytes, Cell Immunol. 176(2):180-5, 1997.

(Continued)

*Primary Examiner* — James D Anderson
(74) *Attorney, Agent, or Firm* — Browdy and Neimark, PLLC

(57) ABSTRACT

Methods for treating skin conditions such as basal cell carcinoma and/or actinic keratosis are provided, which are effected by administering a pharmaceutically effective amount of a tellurium-containing compound. A pharmaceutical composition for treatment of skin conditions such as basal cell carcinoma an/or actinic keratosis is also provided.

6 Claims, No Drawings

(56) References Cited

OTHER PUBLICATIONS

Kalechman et al., Effect of the immunomodulator AS101 on chemotherapy-induced multilineage myelosuppression, thrombocytopenia, and anemia in mice, Exp. Hematol. 23 (13):1358-66, 1995.

Fisher, M. S., et al., Systemic alteration induced in mice by ultraviolet light irradiation and its relationship to ultraviolet carcinogenesis, Proc. Natl. Acad. Sci. 74:1688-1692, 1977.

Gibson et al., Cellular requirements for cytokine production in response to the immunomodulators imiquimod and S-27609, J. Interferon Cytokine Res. 15:537-545, 1995.

Sredni et al., Cytokine secretion effected by synergism of the immunomodulator AS101 and the protein kinase C inducer bryostatin, Immunology 70(4):473-7, 1990.

Kalechman et al., Up-regulation by ammonium trichloro(dioxoethylene-0,0') tellurate (AS101) of Fas/Apo-1 expression on B16 melanoma cells: implications for the antitumor effects of AS101, J Immunol. 161(7):3536-42, 1998.

Sredni et al., Bone marrow-sparing and prevention of alopecia by AS101 in non-small cell lung cancer patients treated with carboplatin and etoposide, J. Clin. Oncol. 13(9):2342-53, 1995.

Kadowaki, N., et al., Subsets of human dendritic cell precursors express different toll-like receptors and respnd to different microbial antigens, J. Exp. Med. 194:863-870, 2001.

Sredni et al., The biological activity and immunotherapeutic properties of AS-101. A synthetic organotellurium compound, Nat. Immun. Cell Growth Regul. 7(3):163-8, 1988.

Shani et al., Immunologic effects of AS101 in the treatment of cancer patients, Nat. Immun. Cell Growth Regul. 9 (3):182-90, 1990.

Sredni et al., A new immunomodulating compound (AS-101) with potential therapeutic application, Nature 330 (6144):173-6, 1987.

Soehnge, H; et al., Mechanisms of induction of skin cancer by UV radiation, Frontiers in Bioscience 2:538-551, 1997.

Suzuki, H., et al., Imiquimod, a topical immune response modifier, induces migration of langerhans cells, J. Invest Dermatol. 114:135-141, 2000.

* cited by examiner

USE OF TELLURIUM COMPOUNDS FOR THE TREATMENT OF ACTINIC KERATOSIS

RELATED APPLICATIONS

This Application is a National Phase of PCT Patent Application No. PCT/IL2006/001080 having International filing date of Sep. 14, 2006, which claims the benefit of U.S. Provisional Patent Application No. 60/716,923 filed on Sep. 15, 2005. The contents of the above Applications are all incorporated herein by reference.

FIELD AND BACKGROUND OF THE INVENTION

The present invention relates to novel therapeutic methods and pharmaceutical compositions for treating skin conditions and, more particularly, to compositions comprising and methods utilizing tellurium-containing compounds for treatment of basal cell carcinoma and/or actinic keratosis.

Basal cell carcinoma (BCC) is the most common form of skin cancer, affecting 800,000 Americans each year, and is, in fact, the most common malignancy in humans. Such carcinomas occur most frequently on the face, ears, neck, scalp, shoulders, and back. BCC is usually slow growing and rarely metastasizes, but it can cause significant local destruction and disfigurement if neglected or treated inadequately.

Contributing factors to BCC include exposure to radiation, such as X-ray exposure; arsenic exposure; immunosuppression; the autosomal-recessive disease, Xeroderma pigmentosum; nevoid BCC syndrome (basal cell nevus syndrome, Gorlin syndrome); Bazex syndrome; and complications of burns, scars, vaccinations, or even tattoos are contributing factors.

BCC is believed to arise from pluripotential cells within the basal layer of the epidermis or follicular structures. These cells form continuously during life and are capable of forming hair, sebaceous glands, and apocrine glands. Tumors usually arise from the epidermis and occasionally arise from the outer root sheath of a hair follicle, specifically from hair follicle stem cells residing just below the sebaceous gland duct.

The mechanism by which BCC develops is believed to include a decrease in Langerhans cells, dendritic epidermal T cells, and Thy1+ cells. Furthermore, systemic proliferation of suppressor T cells and the release of immunosuppressive factors (eg, tumor necrosis factor-a (TNF-α), interleukin-1-β (IL-1), prostaglandin (PG), interleukin 10 (IL-10) are believed to be pathogenic to the development of BCC.

In a large proportion of BCC biopsy specimens, high IL-10 expression has been found. Immunohistochemical evaluation has revealed that IL-10 is specifically localized in BCC tumor-bearing lesions, but not in the normal epidermis or dermis [1, 2]. IL-10 is not expressed in the tumor-infiltrating-lymphocytes (TIL) which attempt to destroy the tumor. Moreover, it has been demonstrated that this TIL population is inactivated by BCC-derived IL-10, resulting in their inability to respond to the tumor. Inactivation of IL-10 by anti-IL-10 neutralizing antibodies restores, in vitro, the anti-BCC TIL recognition. These findings indicate that BCC-derived IL-10 is, at least in part, responsible for immunosuppression of the local immune response. In addition, it has been found that IL-10 serves as a tumor growth factor, which constitutively activates transcription factors needed for cellular proliferation.

Treatment of BCC generally involves use of antineoplastic agents, such as 5-fluorouracil, which interferes with DNA synthesis by blocking methylation of deoxyuridylic acid and inhibiting thymidylate synthetase and, subsequently, cell proliferation; imiquimod, which is believed to increase tumor infiltration of lymphocytes, dendritic cells, and macrophages; interferon α 2-β, which is believed to act via direct antiproliferative effects against malignant cells and modulation of host immune response.

Actinic keratosis is the most common skin growth. Actinic keratoses are chiefly found on the face, the ears, the forearms, and the dorsum of the hands. However, they may occur on other areas such as the back, the chest, and the legs. They usually appear as multiple discrete, flat or elevated, verrucous, keratotic lesions. Lesions typically have an erythematosus base covered by scale (hyperkeratosis). They are usually 3-10 mm in diameter and gradually enlarge into broader, more elevated lesions. Actinic keratoses are pre-cancerous growths, which may develop into squamous cell carcinomas if left untreated.

Actinic keratosis is believed to be associated with decreased expression or activity of cytokine signal regulators. Langerhans cells, situated in the epidermis layer of the skin, have been found to have changed shape and altered function in actinic keratosis. These cells are involved in presenting presentation of antigens to T-cells. Damage to these cells results in an immunosuppressive effect on the skin. Increased incidence of actinic keratosis is found in patients having a weak or suppressed immune system.

Actinic keratosis is most commonly treated with 5-fluorouracil. Other medications include diclofenac sodium and imiquimod.

However, 5-fluorouracil may result in local erythema and hypersensitivity Further common side effects of fluorouracil include extreme fatigue; nausea; mouth sores and ulcer; diarrhea; and temporary drop in bone marrow function, causing a drop in white blood cell count, which increases the risk of severe infection, anemia and drop in blood platelets. Occasional side effects include hair thinning; brittle, chipped and ridged nails; sensitivity of the skin to sunlight; rashes; watery eyes; and loss of appetite.

Imiquimod is not indicated for treatment of tumors of the head or neck, and is not suitable for treatment of tumors of more than 2 cm in diameter. Side-effects of imiquimod include skin infection and skin rash, back pain, burning or itching, changes in skin color, diarrhea, headache, muscle aches, redness of the skin, scabbing and crusting, skin peeling, skin that becomes hard or thickened and swelling of the skin.

Common side-effects of interferon α 2-β include flu-like syndrome with fever, chills, tiredness, headache, muscle and bone aches; decreased appetite, mild nausea, mild diarrhea, seizures, irritability, poor mental concentration, and sleepiness. Less common side effects include changes in taste and dry mouth, dizziness, and abnormal results on kidney function blood tests. Rare side effects include decreased white cell count with increased risk of infection, decreased platelet count with increased risk of bleeding, vomiting, confusion, depression, chest pain, change in blood pressure, partial hair loss, rash, dry throat, irritation at the site of injection, congestive heart failure, impotence and menstrual irregularities. Incidence of severe or fatal gastrointestinal hemorrhage has been reported.

There is thus a widely recognized need for and it would be highly advantageous to have novel treatments for BCC and actinic keratosis, devoid of the above limitations.

Various tellurium compounds have been described in the art as having immunomodulating properties. A particularly effective family of tellurium-containing compounds is taught, for example, in U.S. Pat. Nos. 4,752,614; 4,761,490; 4,764,461 and 4,929,739, whereby another effective family is taught, for example, in a recently filed U.S. Provisional Patent Application No. 60/610,660, which are all incorporated by reference as if fully set forth herein. The immunomodulating properties of this family of tellurium-containing compounds is described, for example, in U.S. Pat. Nos. 4,962,207, 5,093, 135, 5,102,908 and 5,213,899, which are all incorporated by reference as if fully set forth herein.

One of the most promising compounds described in these patents is ammonium trichloro(dioxyethylene-O,O')tellurate, which is also referred to herein and in the art as AS101. AS101, as a representative example of the family of tellurium-containing compound discussed hereinabove, exhibits antiviral (*Nat. Immun. Cell Growth Regul.* 7(3):163-8, 1988; *AIDS Res Hum Retroviruses.* 8(5):613-23, 1992), and tumoricidal activity (*Nature* 330(6144):173-6, 1987; *J. Clin. Oncol.* 13(9):2342-53, 1995; *J Immunol.* 161(7):3536-42, 1998.

It has been suggested that AS101, as well as other tellurium-containing immunomodulators, stimulate the innate and acquired arm of the immune response. For example, it has been shown that AS101 is a potent activator of interferon (IFN) (IFN) in mice (*J. Natl. Cancer Inst.* 88(18):1276-84, 1996) and humans (*Nat. Immun. Cell Growth Regul.* 9(3): 182-90, 1990; *Immunology* 70(4):473-7, 1990; *J. Natl. Cancer Inst.* 88(18):1276-84, 1996.)

It has also been demonstrated that AS101, as well as other tellurium-containing immunomodulators, induce the secretion of a spectrum of cytokines, such as IL-1α, IL-6 and TNF-α, and that macrophages are one main target for AS101 (*Exp. Hematol.* 23(13):1358-66, 1995) and it was found to inhibit IL-10 at the m-RNA level, and this inhibition may cause an increase in IL-12 (*Cell Immunol.* 176(2):180-5, 1997); *J. Natl. Cancer Inst.* 88(18)3276-84, 1996).

Other publications describing the immunomodulation properties of AS101 include, for example, "The immunomodulator AS101 restores T(H1) type of response suppressed by *Babesia rodhaini* in BALB/c mice". *Cell Immunol* 1998 February; "Predominance of TH1 response in tumor-bearing mice and cancer patients treated with AS101". *J Natl Cancer Inst* 1996 September; "AS-101: a modulator of in vitro T-cell proliferation". *Anticancer Drugs* 1993 June; "The immunomodulator AS101 administered orally as a chemoprotective and radioprotective agent". *Int J Immunopharmacol* 1992 May; "Inhibition of the reverse transcriptase activity and replication of human immunodeficiency virus type 1 by AS101 in vitro". *AIDS Res Hum Retroviruses* 1992 May; "Immunomodulatory effects of AS101 on interleukin-2 production and T-lymphocyte function of lymphocytes treated with psoralens and ultraviolet A". *Photodermatol Photoimmunol Photomed* 1992 February; "Use and mechanism of action of AS101 in protecting bone marrow colony forming units-granulocyte-macrophage following purging with ASTA-Z 7557". *Cancer Res* 1991 Oct. 15; "The effect of the immunomodulator agent AS101 on interleukin-2 production in systemic lupus erythematosus (SLE) induced in mice by a pathogenic anti-DNA antibody". *Clin Exp Immunol* 1990 March; "Toxicity study in rats of a tellurium based immunomodulating drug, AS-101: a potential drug for AIDS and cancer patients". *Arch Toxicol* 1989; "The biological activity and immunotherapeutic properties of AS-101, a synthetic organotellurium compound". *Nat Immun Cell Growth Regul* 1988; and "A new immunomodulating compound (AS-101) with potential therapeutic application". *Nature* 1987 November.

In addition to its immunomodulatory effect, AS101 is also characterized by low toxicity. Toxicity tests have shown that LD50 values in rats following intravenous and intramuscular administration of AS101 are 500-1000 folds higher than the immunologically effective dose.

While the immunomodulating effect of tellurium-containing compounds was studied with respect to various aspects thereof, the use of tellurium compounds in the treatment of skin diseases such as basal cell carcinoma and/or actinic keratosis has never been suggested nor practiced hitherto.

SUMMARY OF THE INVENTION

The present invention successfully addresses the shortcomings of the presently known methods of treating skin conditions such as basal cell carcinoma and actinic keratosis by providing methods and compositions comprising tellurium compounds, which are devoid of the side effects of the commonly known treatments for these conditions.

According to one aspect of the present invention there is provided a method of treating a condition of the skin selected from the group consisting of basal cell carcinoma and actinic keratosis in a subject in need thereof, the method comprising administering to a subject a therapeutically effective amount of at least one tellurium-containing compound.

According to another aspect of the present invention there is provided a method of treating basal cell carcinoma, the method comprising administering to a subject a therapeutically effective amount of at least one tellurium-containing compound.

According to yet another aspect of the present invention there is provided a method of treating actinic keratosis, the method comprising administering to the subject a therapeutically effective amount of at least one tellurium-containing compound.

According to still another aspect of the present invention there is provided a use of a tellurium-containing compound in the manufacture of a medicament, whereby the medicament is for treating actinic keratosis and/or treating basal cell carcinoma.

According to an additional aspect of the present invention there is provided pharmaceutical composition identified for use in the treatment of a condition of the skin selected from the group consisting of basal cell carcinoma and actinic keratosis, the composition comprising at least one tellurium-containing compound and a pharmaceutically acceptable carrier.

According to further features in preferred embodiments of the invention described below, the tellurium-containing compound of the present invention is a compound comprising a tellurium dioxide moiety and optionally and preferably is at least one of tellurium dioxide ($TeO_2$) per se, an organic complex of $TeO_2$ (as detailed hereinbelow), a compound having general Formula I:

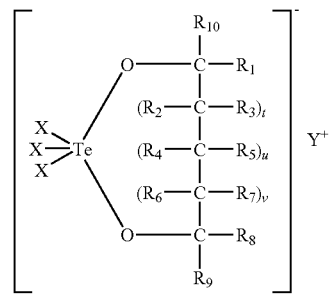

Formula I a compound having general Formula II:

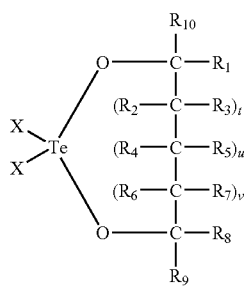

Formula II a compound having general Formula III:

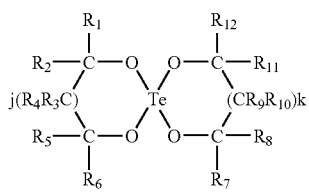

Formula III and
a compound having general Formula IV:

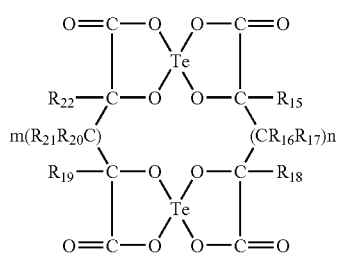

Formula IV wherein:

each of t, u and v is independently 0 or 1;
each of m and n is independently an integer from 0 to 3;
each of j and k is independently an integer from 0 to 4;
Y is selected from the group consisting of ammonium, phosphonium, potassium, sodium and lithium;
X is a halogen atom; and
each of $R_1$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

Preferably, the tellurium-containing compound has general Formula I or general Formula IV.

According to an embodiment in which the tellurium-containing compound has general Formula I, preferably t, u and v are each 0. More preferably, each of $R_1$, $R_8$, $R_9$ and $R_{10}$ is hydrogen; more preferably X is a halogen atom, most preferably the halogen atom is chloro. More preferably, Y is ammonium. The preferred compound according to this embodiment is referred to hereinafter as AS101.

According to an alternative embodiment of this feature of the present invention, the tellurium-containing compound has the general Formula IV. Preferably, according to this embodiment, n and m are each 0. More preferably, each of $R_{15}$, $R_{18}$, $R_{19}$ and $R_{22}$ is hydrogen. The preferred compound according to this embodiment is referred to hereinafter as SAS.

According to still further features in the described preferred embodiments of the methods of the present invention, administering is effected systemically. Preferably, for systemic administration, a therapeutically effective amount of a compound of formula I, II or III ranges from about 0.1 mg/m$^2$/day to about 10.0 mg/m$^2$/day. Also preferably, a therapeutically effective amount of a compound of formula IV ranges from about 0.17 mg/m$^2$/day to about 17 mg/m$^2$/day.

According to still further features in the described preferred embodiments of the methods of the present invention, administering is effected topically, preferably by applying a therapeutically effective amount of a tellurium-containing compound onto a treated skin area.

According to still further features in the described preferred embodiments of the methods, uses or compositions of the present invention, the tellurium-containing compound forms a part of a pharmaceutical composition, further comprising a pharmaceutically acceptable carrier. Preferably, a concentration of tellurium-containing compound of formula I, II or III in the carrier ranges from about 0.01 weight percent to about 50 weight percents, more preferably from about 0.01 weight percent to about 20 weight percents, of the total weight of the composition. Also preferably, a concentration of tellurium-containing compound of formula IV in the carrier ranges from about 0.02 weight percent to about 85 weight percents, more preferably from about 0.02 weight percents to about 40 weight percents of the total weight of the composition.

For topical administration, the pharmaceutical composition is preferably in the form of a cream, an ointment, a paste, a gel, a lotion, a milk, a suspension, a solution, an aerosol, a spray, a foam, a shampoo, a mousse, a serum, a swab, a pledget, a pad, a tincture, a patch or a soap.

Optionally, the pharmaceutical composition may further comprise at least one additional active agent, including, but not limited to, an antineoplastic agent, an immunomodulator, an interferon and a non-steroidal anti-inflammatory drug (such as oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof).

More preferably, the additional active agent is at least one of fluorouracil, imiquimod, interferon-α, and diclofenac.

According to still further features in the described preferred embodiments of the methods, uses or compositions of the present invention, the composition may optionally further comprise at least one ingredient selected from the group consisting of a humectant, a deodorant agent, an antiperspirant, a sun screening agent, a sunless tanning agent, a pH adjusting agent, a chelating agent, a preservative, an emulsifier, an occlusive agent, an emollient, a thickener, a solubilizing agent, a penetration enhancer, an anti-irritant, a colorant, a propellant and a surfactant.

The pharmaceutical composition may be packaged in a packaging material and identified in print, in or on the packaging material, for use in treating a condition of the skin selected from the group consisting of basal cell carcinoma and actinic keratosis.

According to still further features in the described preferred embodiments the carrier is selected such that: the tellurium-containing compound, at a concentration of 10 weight percents, is soluble, dispersible and/or suspendable therein; and the formulation is chemically and physically stable upon storage at room temperature for at least 30 days.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" of means that the composition or method may include additional ingredients and/or steps, but only if the additional ingredients and/or steps do not materially alter the basic and novel characteristics of the claimed composition or method.

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

DESCRIPTION OF THE PREFERRED EMBODIMENTS

The present invention is of methods and compositions comprising tellurium-containing compounds for treatment of skin conditions such as basal cell carcinoma and actinic keratosis.

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention successfully addresses the shortcomings of the presently known methods of treating skin conditions such as basal cell carcinoma and actinic keratosis by providing methods and compositions comprising tellurium compounds, which are devoid of the side effects of the commonly known treatments for these conditions.

The present invention provides a method of treating a condition of the skin such as basal cell carcinoma or actinic keratosis. As mentioned in the Background section hereinabove, the development of BCC and AK is believed to involve cytokine-mediated changes in the immune system, resulting in decreased number or activity of Langherhans cells. Immune-response modifiers have been found to induce activation of Toll-like receptors, which leads to production of cytokines and chemokines, such as INF-[alpha], TNF-[alpha], IL-12, MCP-1, and MIP-1 [alpha] [3, 4]. The chemokines attract immune cells to the site of application, and the cytokines cause activation of immune cells. Toll agonists have been found to promote cytokine and chemokine release from dendritic cells that reside in the dermis and the epidermis [3]. Activation of immune cells and release of cytokines by these dendritic cells can rally the immune system back into action, overcoming the reduced number or activity of Langerhans cells [5].

While conceiving the present invention, it was envisioned that since AS101 is a potent modulator of the immune response, and is further characterized as a substantially non-toxic agent, this tellurium-containing compound, as well as other tellurium compounds of this family, could serve as potent therapeutic agents against skin conditions such as BCC and AK, devoid of the disadvantages associated with the presently known agents for treating these conditions described hereinabove.

As used herein, the phrase "tellurium-containing compound" encompasses any compound that includes one or more tellurium atoms and exhibits immunomodulating properties.

The phrase "immunomodulating properties" includes any effect of the compound on the immune response of a subject. Exemplary immunomodulating properties can be manifested, for example, by an effect on cytokines secretion, interleukins production, lymphocytes function, and the like.

Preferably, the tellurium-containing compound includes at least one tellurium dioxide moiety.

Thus, the compound can be, for example, an inorganic tellurium-containing compound such as, for example, tellurium dioxide ($TeO_2$) per se.

The compound can alternatively be an organic tellurium-containing compound which includes one or more tellurium atoms and one or more organic moieties that are attached thereto.

Representative examples of inorganic tellurium-containing compounds that were shown to exert immunomodulating properties and hence are particularly useful in the context of the present invention include, for example, $TeO_2$ per se. Also included are compounds that form $TeO_2$ in aqueous solutions, preferably in the form of an organic complex such as, for example, a $TeO_2$ complex with citric acid or ethylene glycol. A representative example of the latter is the complex $TeO_2 \cdot HOCH_2CH_2OH \cdot NH_4Cl$.

Organic tellurium-containing compounds that were shown to exert immunomodulating properties and hence are particularly useful in the context of the present invention include, for example, ammonium salts, or any other salts, of halogenated tellurium-containing compounds having a bidentate cyclic moiety attached to the tellurium atom. The bidentate cyclic moiety is preferably a di-oxo moiety having two oxygen atoms attached to the tellurium atom. Alternatively, the bidentate cyclic moiety can be a di-thio moiety, in which two sulfur atoms are attached to the tellurium atom.

Preferred compounds in this category are collectively represented by the general Formula I:

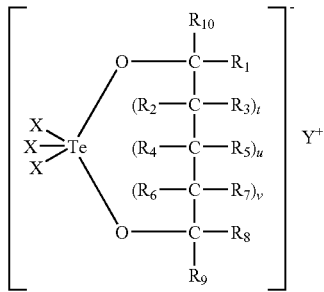

Formula I

In the general Formula I above, each of t, u and v is independently 0 or 1, such that the compound may include a five-membered ring, a six-membered ring, or a seven-membered ring. Preferably, each of t, u and v is 0, such that the compound includes a five-membered ring.

X is a halogen atom, as described hereinabove, and is preferably chloro.

Y is selected from the group consisting of ammonium, phosphonium, potassium, sodium and lithium, and is preferably ammonium.

each of $R_1$-$R_{10}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfonyl, sulfate, amine, aryl, heteroaryl, phosphate, phosphonate and sulfonamido.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "haloalkyl" refers to an alkyl, as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, —$CH_2CONH_2$; —$CH_2CH_2CONH_2$; —$CH_2CH_2CH_2CONH_2$ and the like.

The term "cyanoalkyl" refers to an alkyl, as this term is defined herein, substituted by an cyano group, as defined herein, and includes, for example, —$CH_2CN$; —$CH_2CH_2CN$; —$CH_2CH_2CH_2CN$ and the like.

The term "N-monoalkylamidoalkyl" refers to an alkyl, as this term is defined herein, substituted by an amide group, as defined herein, in which one of R' and R" is an alkyl, and includes, for example, —$CH_2CH_2CONHCH_3$, and —$CH_2CONHCH_2CH_3$.

The term N,N-dialkylamidoalkyl refers to an alkyl, as this term is defined herein, substituted by an amide group, as defined herein, in which both R' and R" are alkyl, and includes, for example, —$CH_2CON(CH_3)_2$; $CH_2CH_2CON(CH_2$—$CH_3)_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, phosphonyl, phosphinyl, carbonyl, thiocarbonyl, carboxy, thiocarboxy, carbamate, thiocarbamate, amido, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein. Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "carboxy" group refers to a —C(=O)—O—R' or a —O—C(=O)—R' group, where R' is as defined herein.

A "sulfinyl" group refers to an —S(=O)—R' group, where R' is as defined herein.

A "sulfonyl" group refers to an —S(=O)$_2$—R' group, where R' is as defined herein.

A "sulfate" group refers to a —O—S(=O)$_2$—OR' group, where R' is as defined herein.

A "sulfonamido" group refers to a —S(=O)$_2$—NR'R" group or a R'S(=O)$_2$—NR", with R' is as defined herein and R" is as defined for R'.

A "carbamyl" or "carbamate" group refers to an —OC(=O)—NR'R" group or a R"OC(=O)—NR'— group, where R' and R" are as defined herein.

A "thiocarbamyl" or "thiocarbamate" group refers to an —OC(=S)—NR'R" group or an R"OC(=S)NR'— group, where R' and R" are as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

A "nitro" group refers to an —NO$_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

As cited hereinabove, the compounds in this category are salts of organic tellurium-containing compounds. The salts can be, for example, ammonium salts, phosphonium salts and alkaline salts such as potassium salts, sodium salts, lithium salts and the like.

Hence, Y in Formula I above can be a phosphonium group, as defined herein, an ammonium group, as defined herein, potassium ($K^+$), sodium ($Na^+$) or lithium ($Li^+$).

As used herein, the term "phosphonium" describes a —$P^+$R'R"R'" group, with R' and R" as defined herein and R'" is as defined for R'. The term "phosphonium", as used herein, further refers to a —$P^+R_6$ group, wherein each of the six R substituents is independently as defined herein for R, R" and R'".

The term "ammonium" describes a —$N^+$R'R"R'" group, with R', R" and R'" as defined herein.

More preferred compounds in this category include compounds having the general Formula I described above, in which Y is ammonium or phosphonium, t, u and v are each 0, and each of $R_1$, $R_8$, $R_9$ and $R_{10}$ is independently hydrogen or alkyl. These compounds can be represented by the following structure:

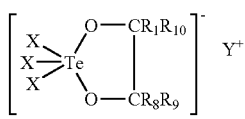

wherein each of $R_1$, $R_8$, $R_9$ and $R_{10}$ is independently hydrogen or alkyl, whereas a preferred alkyl is methyl, and X is halogen, preferably chloro.

The presently most preferred compound for use in the context of the present invention has the following structure:

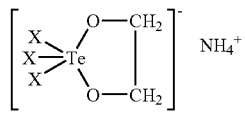

This compound is ammonium trichloro(dioxyethylene-O, O')tellurate, which is also referred to herein and in the art as AS101.

Additional representative examples of organic tellurium-containing compound that are suitable for use in the context of the present invention include halogenated tellurium having a bidentate cyclic moiety attached to the tellurium atom. The bidentate cyclic moiety is preferably a di-oxo ligand having two oxygen atoms attached to the tellurium atom. Alternatively, the bidentate cyclic moiety can be a di-thio ligand, in which two sulfur atoms are attached to the tellurium atom.

Preferred compounds in this category can be represented by the general Formula II:

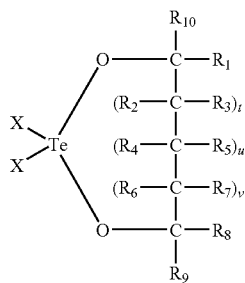

Formula II wherein t, u, v, X and $R_1$-$R_{10}$ are as defined hereinabove.

More preferred compounds are those in which t, u, and v are each 0, and X is chloro, such as, but not limited to, the compound having the following structure:

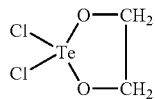

The above compound is also known and referred to herein as AS103.

The organic tellurium-containing compounds having Formulae I and II can be readily prepared by reacting tetrahalotelluride such as $TeCl_4$ with a dihydroxy compound, as is described in detail in U.S. Pat. Nos. 4,752,614, 4,761,490, 4,764,461 and 4,929,739, which are incorporated by reference as if fully set forth herein.

Additional representative examples of organic tellurium-containing compounds that are suitable for use in the context of the present invention include compounds in which two bidentate cyclic moieties are attached to the tellurium atom. Preferably, each of the cyclic moieties is a di-oxo moiety. Alternatively, one or more of the cyclic moieties is a di-thio moiety.

Preferred compounds in this category are collectively represented by the general Formula III:

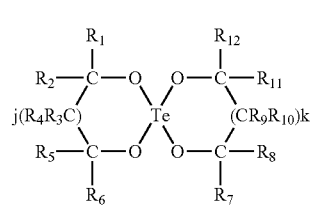

Formula III

In the general Formula III above, each of j and k is independently an integer from 0 to 4, such that the compound may include a five-membered ring, a six-membered ring, a seven-membered ring, an eight-membered ring and/or a nine-membered ring. Preferably, each of j and k is an integer from 0 to 2, such that the compound includes a five-membered ring, a six-membered ring and/or a seven-membered ring. More preferably, each of j and k is 0.

$R_1$-$R_{12}$ are as defined hereinabove for $R_1$-$R_{10}$.

More preferred compounds in this category are those in which j and k are each 0, and $R_3$, $R_4$, $R_9$ and $R_{10}$ are each hydrogen, having the following structure:

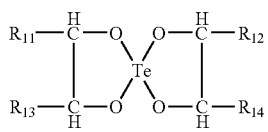

wherein each of $R_{11}$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido, as these terms are defined herein.

The most preferred compound in this category is a compound in which each of $R_{11}$-$R_{14}$ is hydrogen. This compound is also known as AS102.

Additional representative examples of organic tellurium-containing compounds that are suitable for use in the context of the present invention include the recently disclosed bis-tellurium compounds having general Formula IV:

Formula IV

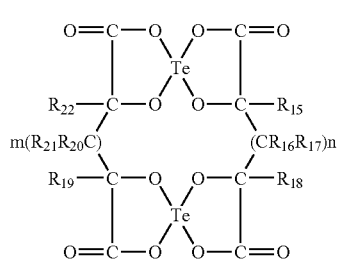

wherein each of $R_{15}$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido, as these terms are defined herein; and m and n are each an integer from 0 to 3.

Preferred compounds in this category are those in which m and n are each 0.

The presently most preferred compound in this family is a compound in which $R_{15}$, $R_{18}$, $R_{19}$ and $R_{22}$ are all hydrogen, referred to hereinafter as SAS, and which has the following structure:

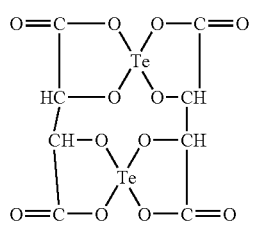

Compounds having the general Formula IV can be readily prepared by reacting substantially equimolar amounts of a tellurium tetralkoxide and a polycarboxylic acid. These materials are combined in the presence of a water free organic solvent such as dried ethanol, dimethyl sulfoxide, i-propanol and the like. Generally the reaction may take place at ambient conditions but if desired higher or lower temperatures and higher or lower pressures may be utilized.

Exemplary tellurium tetraalkoxide compounds that are usable in the preparation of the compounds having general Formula IV above include, without limitation, tetramethoxide, tetraethoxide, tetrapropoxide, tetraisopropoxide, tetrabutoxide, and tetrapentoxide tellerium compounds.

Useful polycarboxylic acids include also polyhydroxy polycarboxylic and hydroxy polycarboxylic acids. Exemplary polycarboxylic acids that are usable in the preparation of the compounds having general Formula IV above include, without limitation, tartaric acid, glutaric acid, succinic acid, malonic acid, gluconic acid and the like.

Additional organic tellurium-containing compounds that are suitable for use in the context of the present invention include those having the general Formula V:

Formula V

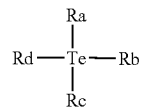

wherein each of Ra, Rb, Rc and Rd is independently selected from the group consisting of halogen alkyl, aryl, cycloalkyl, alkoxy, aryloxy, thioalkoxy, thioaryloxy, carboxy, carbonyl, thiocarboxy, thiocarbonyl, carbamyl, and thiocarbamyl, as these terms are defined hereinabove, whereby at least one of Ra-Rd is not halogen, namely, is selected from the group consisting of alkyl, aryl, cycloalkyl, alkoxy, aryloxy, thioalkoxy, thioaryloxy, carboxy, carbonyl, thiocarboxy, thiocarbonyl, carbamyl, and thiocarbamyl.

Compounds in this category include those in which one of Ra, Rb, Rc and Rd is halogen alkyl, aryl, cycloalkyl, alkoxy, aryloxy, thioalkoxy, thioaryloxy, carboxy, carbonyl, thiocarboxy, thiocarbonyl, carbamyl, or thiocarbamyl, whereby the others are halogen atoms, e.g., chloro.

Other compounds in this category include those in which two or three of Ra, Rb, Rc and Rd are as described above and the others are halogens e.g., chloro.

Other compounds in this category include those in which each of Ra, Rb, Rc and Rd is as described hereinabove.

The compounds described above can be administered or otherwise utilized in this and other aspects of the present invention, either as is or as a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The compounds described above can be administered to a subject afflicted by a skin condition such as BCC or AK by any of various systemic routes.

Suitable routes of systemic administration may, for example, include the inhalation, oral, buccal, rectal, transmucosal, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

Optionally and preferably, the compounds described above can be administered to a subject afflicted by a skin condition such as BCC or AK by local routes, and more preferably, the compounds are administered topically.

Topical application of the tellurium-containing compounds described herein is preferably effected by applying a therapeutically effective amount of a tellurium-containing compound onto a treated skin area.

The treated area can be, for example, an area of the face, ears, neck, scalp, shoulder, back, forearm, hand, chest or leg.

Herein, the phrase "treated area" encompasses the affected area as well as the tissues surrounding the indicated area. The topical application is effected on and around the clinical manifestation.

The term "therapeutically effective amount" or "pharmaceutically effective amount" denotes that dose of an active ingredient or a composition comprising the active ingredient that will provide the therapeutic effect for which the active ingredient is indicated. Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

When administering systemically, a therapeutically effective amount of the tellurium-containing compounds described herein may range, for example, from about 0.01 mg/m$^2$/day to about 20.0 mg/m$^2$/day and thus can be for example, 0.01 mg/m$^2$/day, 0.02 mg/m$^2$/day, 0.03 mg/m$^2$/day, 0.04 mg/m$^2$/day, 0.05 mg/m$^2$/day, 0.1 mg/m$^2$/day, 1 mg/m$^2$/day, 2 mg/m$^2$/day, 3 mg/m$^2$/day, 4 mg/m$^2$/day, 5 mg/m$^2$/day, 10 mg/m$^2$/day, and up to 20 mg/m$^2$/day. Preferably, for systemic administration, a therapeutically effective amount of a compound of formula I, II or III ranges from about 0.1 mg/m$^2$/day to about 20 mg/m$^2$/day. Also preferably, a therapeutically effective amount of a compound of formula IV for systemic administration ranges from about 0.017 mg/m$^2$/day to about 17 mg/m$^2$/day.

Preferably, when administered parenterally, the therapeutically effective amount is 0.1 mg/m$^2$/day and higher and thus can be, for example, 0.2 mg/m$^2$/day, 0.3 mg/m$^2$/day, 0.4 mg/m$^2$/day, 0.5 mg/m$^2$/day, 0.6 mg/m$^2$/day, 0.7 mg/m$^2$/day, 0.8 mg/m$^2$/day, 0.9 mg/m$^2$/day, 1.0 mg/m$^2$/day, 2.0 mg/m$^2$/day, 3.0 mg/m$^2$/day, 4.0 mg/m$^2$/day, 5.0 mg/m$^2$/day, and up to 20.0 mg/m$^2$/day.

When administered orally in humans, a daily dose typically ranges between 0.1 mg and 200 mg, more preferably between 1 mg and 100 mg and more preferably between 1 mg and 10 mg. The total daily dose may be administered as a single dosage, or may be divided into a number of separate doses, such as, for example 5 mg twice daily, 2.5 mg twice daily.

As used herein, the term "about" refers to ±10%.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The method according to this aspect of the present invention can further comprise, in addition to administering the tellurium-containing compounds described above, co-administration of an additional active agent. The co-administration can be effected prior to, concomitant with or subsequent to the administration of the tellurium-containing compound. The additional active agent is used for providing an additive beneficial effect in terms of the ailment being treated, conditions associated with the ailment being treated or other parameters such as psychological effects and prophylactic effects.

Hence, exemplary additional active agents according to this embodiment of present invention include, without limitation, one or more, or any combination of an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, a suitable anti-oxidant, an antineoplastic agent, an immunomodulator, an interferon, an antidepressant, an anti histamine, a vitamin, a hormone and an anti-dandruff agent.

Suitable anti-acne agents for use in this context of the present invention include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy propanol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs), corticotropin-releasing factor (CRF) antagonists, α-adrenoreceptor antagonists, NK1-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norelolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B$_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in context of the present invention include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

More preferably, the additional active agent is at least one of fluorouracil, imiquimod, interferon-α, and diclofenac.

In addition to the above, the treatment of skin condition such as BCC or AK according to the present invention may be combined with other treatment methods known in the art (i.e., combination therapy). Thus, the method according to this aspect of the present invention may further involve additional treatment by any of the methods described above for treating BCC or AK, as well as similar skin conditions. The tellurium-containing compounds described above can thus be, for example, co-administered (simultaneously or separately) with additional agents for treating BCC or AK, such as 5-fluorouracil, imiquimod, and the like.

In any of the different embodiments of the method of the present invention, the tellurium-containing compounds described herein can be provided to a subject either per se, or as part of a pharmaceutical composition where it is mixed with a pharmaceutically acceptable carrier.

Hence, according to another aspect of the present invention there is provided a pharmaceutical composition, which comprises a tellurium-containing compound as described herein and a pharmaceutically acceptable carrier.

Preferably, a concentration of tellurium-containing compound of formula I, II or III in the carrier ranges from about 0.01 weight percent to about 50 weight percents, more preferably from about 0.1 weight percents to about 20 weight percents, of the total weight of the composition. Also preferably, a concentration of tellurium-containing compound of formula IV in the carrier ranges from about 0.02 weight percent to about 85 weight percents, more preferably from about 0.2 weight percents to about 40 weight percents of the total weight of the composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise glass, plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Hence, in a preferred embodiment of the present invention, the pharmaceutical composition is formulated in a form suitable for topical application on the treated area.

By selecting the appropriate carrier and optionally other ingredients that can be included in the composition, as is detailed hereinbelow, the compositions of the present invention may be formulated into any form typically employed for topical application. Hence, the compositions of the present invention can be, for example, in a form of a cream, an ointment, a paste, a gel, a lotion, a milk, a suspension, an aerosol, a spray, a foam, a shampoo, a hair conditioner, a serum, a swab, a pledget, a pad, a patch and a soap.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semi-liquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition.

Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions.

Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

When the pharmaceutical composition according to the present invention is formulated for topical application, the concentration of the tellurium-containing compound of formula I, II or III preferably ranges from about 0.01 weight percent and about 50 weight percents, and the concentration of the tellurium-containing compound of formula IV preferably ranges from about 0.02 to about 85 weight percents, of the total weight of the composition.

Thus, depending on the condition being treated and the composition form, the concentration of the tellurium-containing compound can be, for example, 0.01 weight percent, 0.05 weight percent, 0.1 weight percent, 0.5 weight percent, 1 weight percent, 2 weight percents, 3 weight percents, 4 weight percents or 5 weight percents. Higher concentrations can also be used and thus can be, for example, 5 weight percents, 6 weight percents, 7 weight percents, 8 weight percents, 9 weight percents or 10 weight percents and up to 20 weight percents, 25 weight percents, 30 weight percents, 40 weight percents, 50 weight percents, 60 weight percents, 70 weight percents, 80 weight percents, and can be up to 85 weight percents of the total weight of the composition.

A formulation of a tellurium-containing compound, which is particularly useful for topical application of the active compound, and more particularly, for obtaining stable compositions that comprise relatively high concentration of a tellurium-containing compound, has been recently designed by the present assignee. This formulation is described in detail in a U.S. Provisional Patent Application filed Sep. 11, 2006, having Ser. No. 60/843,402 and entitled "Topical Formulations of tellurium-containing compounds", to the present assignee, which is incorporated by reference as if fully set forth herein. This formulation is based on a carrier selected such that: the tellurium-containing compound, at a concentration of 10 weight percents, is soluble, dispersible and/or suspendable therein; and the formulation is chemically and physically stable upon storage at room temperature for at least 30 days.

Hence, in preferred embodiments of the present invention, any of the pharmaceutical compositions described herein comprises a carrier as described in the above-mentioned U.S. Provisional Patent Application filed Sep. 11, 2006, having Ser. No. 60/843,402.

Each of the pharmaceutical compositions described herein may further comprise, according to an embodiment of the present invention an additional active agent, as described hereinabove.

Each of the pharmaceutical compositions described herein can optionally further comprise a variety of components that are suitable for providing the compositions with additional usage benefits. Such conventional optional components are well known to those skilled in the art and are referred to herein as "ingredients". Some non-limiting representative examples of these ingredients include humectants, deodorants, antiperspirants, sun screening agents, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants (and surfactants.

Thus, for example, the compositions of the present invention can comprise humectants or moisturizing agents. Representative examples of humectants that are usable in this context of the present invention include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

The compositions of the present invention can further comprise a pH adjusting agent. The addition of a pH-adjusting agent is particularly preferred when the compositions are applied topically on the skin. The pH of these treated areas is typically lower than 6.0. Hence, it is preferable for the compositions of the present invention to have a pH value of between about 4 and about 7, preferably between about 4 and about 6, so as to avoid irritations to the skin or induction of imbalance of the bacteria population if the genital areas. Suitable pH adjusting agents include, for example, one or more of adipic acids, glycines, citric acids, calcium hydroxides, magnesium aluminometasilicates, buffers or any combinations thereof.

Representative examples of deodorant agents that are usable in the context of the present invention include, without limitation, quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sun screening agents usable in context of the present invention include, without limitation, p-aminobenzoic acid, salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoyl-methane, and any combination thereof.

Representative examples of sunless tanning agents usable in context of the present invention include, without limitation, dihydroxyacetone, glyceraldehyde, indoles and their derivatives. The sunless tanning agents can be used in combination with the sunscreen agents.

The chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

Suitable preservatives that can be used in the context of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

Suitable emulsifiers that can be used in the context of the present invention include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents that can be used in the context of the present invention include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients, that can be used in the context of the present invention include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers usable in context of the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

The compositions of the present invention may be packed or presented in any convenient way. For example, they may be packed in a tube, a bottle, or a pressurized container, using techniques well known to those skilled in the art and as set forth in reference works such as Remington's Pharmaceutical Science 15$^{th}$ Ed. It is preferred that the packaging is done in such a way so as to minimize contact of the unused compositions with the environment, in order to minimize contamination of the compositions before and after the container is opened.

The compositions are preferably identified in print, in or on the packaging material, for use in the treatment of a skin condition such as BCC or AK, as described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Assessment of the Effect of Tellurium Compounds on Basal Cell Carcinoma

The in vivo effects of the compounds of the invention can be assayed through various animal models known to those of ordinary skill in the art. Generally such assays involve the injection of a carcinoma cell line, of mouse or preferably, human, origin, into a cohort of mice.

In most experiments, two groups of experimental mice are studied: a first, control, group which receives only the cell line but no tellurium compound, and a second, test, group which receives the tellurium compound. This second group is divided into several subgroups each of which receives a different dose of the compound, preferably between 10 µg and 100 µg per day for 10-20 days. On these days, the control group will be administered control doses containing only vehicle with no active agent.

The tellurium compounds may be administered at the time of inoculation of the malignant cells, shortly thereafter or following initiation of the disease. Similarly, any additional therapeutic agent may be administered after the inoculation, but before the full development of the tumor mass. In these ways, the effects of agents on different stages of malignant growth and metastasis can be tested.

For assessment of the effect of tellurium compounds on basal cell carcinoma, human basal cell carcinoma cells are administered either subcutaneously or submucosally into mice. Primary tumor growth, survival time, resistance to tumor challenge, cellular infiltrates characteristic of such tumors, and extent of tumor angiogenesis are all parameters of interest which can be evaluated. After 21 days, tumor growth is generally established and the effects of the test agent after this point can be compared to vehicle-alone.

Example 2

Assessment of the Effect of Tellurium Compounds on Actinic Keratosis

Female, 6-7 weeks old, hairless albino mice (skh-1) are used.

Mice are divided into three groups containing 5-14 mice per group. A first group is treated with a composition comprising AS101. A second group is treated with a composition comprising SAS. Each treatment consists of a single topical application of the composition over a 2 cm$^2$ area on the dorsal surface. Each composition comprises the tellurium compound and a pharmaceutically acceptable carrier. A third group of mice, serving as control, is treated with the carrier alone.

After 15 min. following application, the mice are irradiated with x-rays. Exposure of mice is repeated three times a week for a total of 20 weeks. The skin thickness of mice, and papillary skin lesions greater than 1 mm in diameter are measured and recorded twice every week and the average of the two measurements used in the calculations. At the end of the study, 5-19 lesions from each group are randomly biopsied, and fixed in 10% buffered formalin. Formalin-fixed specimens are embedded in paraffin blocks, sectioned at 4 μm thickness, and stained in haematoxylin-eosin.

Example 3

Assessment of the Treatment by Tellurium Compounds of BCC and/or AK-Human Studies Double-blind, randomized studies are carried out on patients with histologically confirmed, visible multiple actinic keratoses and/or basal cell carcinoma. A topical composition comprising AS101 (4 percents) or SAS (7-8 percents) is applied to affected areas once daily, three times per week, and washed off the next day, after around 10 hours of exposure. Treatment is continued for 6 weeks. The effect on patients receiving AS101 is evaluated and compared to that seen in patients receiving placebo.

For evaluation of the effect on actinic keratosis, clearance of AK lesions is clinically and histologically assessed. Efficacy is assessed by lesion number scores and lesion total thickness scores, as determined prior to commencement of treatment and again at 6 week post-treatment. The reduction of keratoses from baseline is calculated.

For evaluation of the effect on basal cell carcinoma, a blood sample is taken prior to treatment, and the skin lesion is examined, measured, and photographed. Two punch skin biopsies are taken from the area of the carcinoma prior to treatment. One sample is examined to confirm the diagnosis of basal cell carcinoma; the other sample undergoes histological testing. A second punch biopsy and fine needle aspiration is taken at the conclusion of the treatment period and subjected to histological analysis. The entire lesion is then surgically removed and examined for skin cancer cells.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited within the Text

1. Soehnge, H; et al. *Frontiers in Bioscience* 2: 538-551, 1997.
2. Freedberg, I. M., et al, eds. Fitzpatrick's Dermatology in General Medicine. Vol 1, 2. 5th ed. New York, N.Y.: McGraw-Hill; 1999.
3. Fisher, M. S., et al. *Proc. Natl. Acad. Sci.* 74:1688-1692, 1977.
4. Kadowaki, N., et al. *J. Exp. Med.* 194:863-870, 2001.
5. Gibson, S. J, et al. *J. Interferon Cytokine Res.* 15:537-545, 1995.
6. Suzuki, H., et al. *J. Invest Dermatol.* 114:135-141, 2000.

What is claimed is:

1. A method of treating actinic keratosis in a subject in need thereof, the method comprising administering to the subject a therapeutically effective amount of at least one tellurium-containing compound selected from the group consisting of tellurium dioxide ($TeO_2$), a complex of $TeO_2$, a compound having general Formula I:

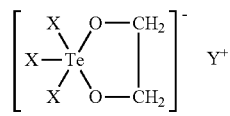

Formula I and a compound having general Formula II:

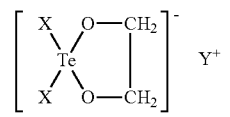

Formula II wherein:
Y is selected from the group consisting of ammonium, phosphonium, potassium, sodium and lithium; and
X is a halogen atom.

2. The method of claim 1, wherein X is chloro.
3. The method of claim 2, wherein Y is ammonium.
4. The method of claim 1, wherein said administering is effected systemically.
5. The method of claim 1, wherein said administering is effected topically.
6. The method of claim 1, wherein said tellurium-containing compound is ammonium trichloro(dioxyethylene-O,O') tellurate.

\* \* \* \* \*